United States Patent
Solomon et al.

[11] Patent Number: 5,861,559
[45] Date of Patent: Jan. 19, 1999

[54] DOUBLE CANTILEVER BEAM CRACK GROWTH SENSOR

[75] Inventors: Harvey Donald Solomon, Niskayuna, N.Y.; Daniel Weinstein, San Jose, Calif.; Ronald Edward DeLair, Niskayuna, N.Y.

[73] Assignee: General Electric Company, Schenectady, N.Y.

[21] Appl. No.: 953,457

[22] Filed: Oct. 17, 1997

[51] Int. Cl.⁶ .................................................. G01N 19/00
[52] U.S. Cl. ............................................. 73/799; 73/821
[58] Field of Search ........................................ 73/799, 821

[56] References Cited

U.S. PATENT DOCUMENTS

| | | |
|---|---|---|
| 4,677,855 | 7/1987 | Coffin, Jr. et al. . |
| 4,818,471 | 4/1989 | Thompson et al. . |
| 4,924,708 | 5/1990 | Solomon et al. ........................... 73/799 |
| 5,317,925 | 6/1994 | Hayashi et al. ............................ 73/799 |
| 5,349,869 | 9/1994 | Diaz et al. . |
| 5,378,429 | 1/1995 | Hayashi et al. ............................ 73/799 |
| 5,386,442 | 1/1995 | Diaz et al. . |
| 5,417,116 | 5/1995 | Solomon et al. ........................... 73/799 |
| 5,556,596 | 9/1996 | Hayashi et al. ............................ 73/799 |

Primary Examiner—Max H. Noori
Attorney, Agent, or Firm—Noreen C. Johnson; Douglas E. Stoner

[57] ABSTRACT

A double cantilever beam (DCB) assembly is disclosed, comprising a fracture specimen having a notch which defines first and second spaced, substantially parallel, outwardly extending beams, terminating at a closed end where crack growth occurs and extending to an open end. The beams are connected to each other along at least a portion of a facing surface of each beam by two, substantially parallel ligaments, spaced from each other on the facing surfaces of the beams. Another disclosed embodiment is a corrosive environment measuring apparatus, comprising a double cantilever beam assembly disposed in an aqueous portion of a reactor vessel, and including the features described above. The reactor vessel is often a constituent of a nuclear reactor, and the DCB assembly is often disposed in a tube which is selectively lowered into the aqueous portion of the reactor vessel. The tube is usually a local power range monitor tube.

20 Claims, 2 Drawing Sheets

DOUBLE CANTILEVER BEAM CRACK GROWTH SENSOR

TECHNICAL FIELD

This invention relates generally to devices for measuring stress corrosion cracking (SCC) in structured materials. More specifically, it relates to double cantilever beam crack growth sensors which are often used to measure SCC for metallic materials used in an aqueous environment.

BACKGROUND OF THE INVENTION

Structural materials which are exposed to aggressive environments are susceptible to cracking. This is particularly the case when the materials are subjected to various levels of cyclic or steady stress, and the resulting occurrence is often referred to as "stress corrosion cracking" or "corrosion fatigue". The nuclear industry has encountered this problem when structural materials (such as stainless steel piping) operate under sustained or cyclic stress in the presence of high temperature water. As described in U.S. Pat. No. 5,417,116 (Solomon et al.), damage from stress corrosion cracking is of greater concern than damage caused by uniform corrosion, since material failure in the first instance is far less predictable than in the second instance. Thus, methods for accurately and conveniently measuring the cracking phenomenon are of great importance.

One very useful technique for measuring crack growth in a corrosive environment involves the use of a double cantilever beam (DCB) sensor. These sensors usually include a pair of elongate beam portions opposed to each other, and a crack growth section formed in a connecting ligament between the beam portions, extending from an axially intermediate portion of each beam portion to a rear end thereof. As described in U.S. Pat. No. 5,378,429 (Hayashi et al.), a pre-cracking section is first formed in the starting end of the crack growth section. Crack growth is measured by a direct current potential method. Wedges inserted between the beam portions, or similar devices, are often used to maintain a selected stress intensity factor at the crack growth section. The Solomon and Hayashi patents provide illustrations of typical DCB sensors, as do U.S. Pat. No. 4,924,708 (Solomon et al.) and U.S. Pat. No. 4,677,855 (Coffin et al.). In the case of the nuclear industry, DCB sensors are often used in a boiling water reactor (BWR). The sensors are placed, for example, inside the pressure vessel of the reactor, in a position exposed to the flow of recirculation water.

A more specific description of the placement of the sensor should be preceded by a brief description of relevant components of a BWR. As those skilled in the art understand, BWR's and other types of reactors include a plurality of fuel rods grouped together to form a fuel assembly. A number of these assemblies are typically arranged in a matrix to form a reactor core. In BWR's, the fuel assemblies are usually grouped in clusters of four, with a control rod associated with each cluster. The control rods—provided with strong neutron-absorbing materials—serve to maintain control of the power level of the reactor. The control rods (or control "blades") in a BWR are often cruciform-shaped.

As described in U.S. Pat. No. 4,818,471 (Thomson et al.), strings of local power range monitors (LPRMs) are typically dispersed throughout the core of a BWR, between the corner locations of the fuel assemblies. Each string includes a hollow tube with multiple neutron detectors located at discrete axial locations. These detectors provide crucial local power monitoring information during operation of the reactor. Movable tip probes are used to calibrate the detectors at specific time intervals. The tip probes (sometimes referred to as "tip tube monitors") are usually inserted into selected detector string tubes from the bottom of the reactor core.

The cross-sectional size of a typical LPRM tube is usually not large enough to accommodate both a DCB sensor and a tip tube monitor. Thus, if a DCB sensor is inserted, a tip tube monitor usually cannot also be used in that tube. The loss of a site for the tip tube monitor would be a serious problem, because of the loss of local power monitoring information which would result from such a reactor design.

One possible way to overcome this problem is to reduce the size of the DCB sensor, which typically has a width of about 1.1–1.5 cm, and a height of about 2.5 cm–3.5 cm (dimensions "W" and "H" in FIG. 1, respectively). However, when the sensor is made smaller than those dimensions, the thickness of the ligament joining the beam portions must also be reduced. It thus becomes very difficult to manufacture and handle sensors with such thin ligaments. Even if a way is found to handle the small sensors, their fragile nature makes them susceptible to breakage. This in turn results in the inability to measure crack growth in a particular location, e.g., within a reactor vessel. Moreover, it is very costly to remove and replace sensors which break during operation of an apparatus like a BWR.

It should thus be apparent that new techniques for incorporating both a DCB sensor and a tip tube monitor into cavities like an LPRM tube would be welcome in the art. If these techniques involve reducing the size of the sensor, they must also involve maintaining its strength and durability. Moreover, a sensor having a reduced size must still fully perform its intended function, i.e., accurately measuring the crack growth of a metal in an aggressive environment. The sensor must also be fully compatible with any attached or surrounding components, and must be relatively easy to produce and incorporate into other equipment, such as an LPRM tube.

SUMMARY OF THE INVENTION

The needs set forth above have been satisfied by the discoveries upon which the present invention is based. One aspect of the invention is directed to a double cantilever beam (DCB) assembly, comprising a fracture specimen having a notch which defines first and second spaced, substantially parallel, outwardly extending beams, terminating at a closed end where crack growth occurs, and extending to an open end. The beams are connected to each other along at least a portion of a facing surface of each beam by two substantially parallel ligaments, spaced from each other on the facing surfaces of the beams. Usually, the ligaments and the beams are formed from the same block of metal, e.g., stainless steel, zirconium alloys, or nickel alloys. In some preferred embodiments of this invention, the size of the DCB sensor is substantially smaller than that of the prior art.

The double cantilever beam assembly can also include other features commonly associated with such a device, such as sensor means positioned along (or incorporated into) the spaced beams, for measuring a voltage drop across the crack when a voltage is applied to the fracture specimen. As described below, the assemblies may also include various means for exerting a load that urges the beams apart from each other at the open end.

The use of two joining ligaments, in contrast to a single, relatively thin ligament, provides strength and durability to the DCB assembly. Thus, smaller assemblies can be constructed and easily handled, leading to the advantages discussed above.

Another aspect of this invention relates to a corrosive environment measuring apparatus, comprising a double cantilever beam assembly disposed in an aqueous portion of a reactor vessel. The DCB assembly comprises:

a fracture specimen having a notch which defines first and second spaced, substantially parallel, outwardly extending beams, terminating at a closed end where crack growth occurs, and extending to an open end;

wherein the beams are connected to each other along at least a portion of a facing surface of each beam by two substantially parallel ligaments, spaced from each other on the facing surfaces of the beams.

The reactor vessel is usually a constituent of a nuclear reactor, and the DCB assembly is often disposed in a tube which is selectively lowered into the aqueous portion of the reactor vessel. In this embodiment, the tube is usually a local power range monitor tube.

Numerous other details regarding these and other embodiments of the present invention are provided below.

DETAILED DESCRIPTION OF THE INVENTION

The general features of DCB sensors are well-known in the art, and described in a variety of references. Examples include the text *Elastic & Plastic Fracture*, by A. G. Atkins et al., 1985, Ellis Horwood, as well as the following U.S. Patents, all of which are incorporated herein by reference: U.S. Pat. Nos. 5,417,116; 5,386,442; 5,378,429; 5,349,869; 5,317,925; 4,924,708; and 4,677,855. All of the conventional features associated with DCB sensors do not need to be described here. Instead, this disclosure relates to those features which are particularly relevant to the claimed invention.

Figure 1:
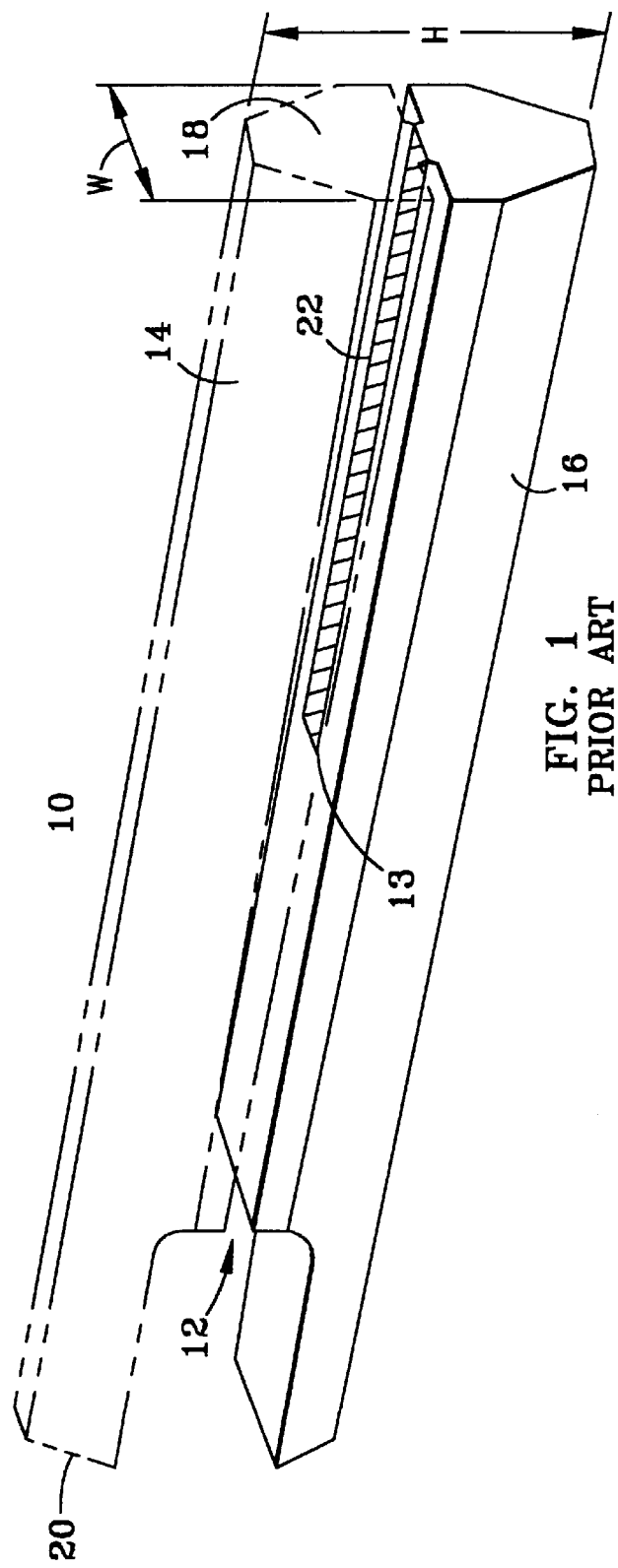
FIG. 1 is a partial perspective view of a DCB sensor of the prior art.

FIG. 1 depicts a typical DCB sensor of the prior art. The figure is a partial perspective view, in which some features are shown in phantom, as described below. The primary metal portion 10 of the sensor assembly is often referred to as a "fracture specimen". It includes a notch 12, which defines outwardly extending beams 14 and 16. The fracture specimen can be made of practically any metal or metal alloy. Non-limiting examples include various types of steel, e.g., carbon steel, stainless steel, and low alloy steel, as well as other high performance-metallic materials, such as zirconium-based alloys and nickel-based alloys. The selection of a particular material will of course be based on its intended use. For example, if the potential effect of hot water or other media on a stainless steel reaction vessel needs to be determined or monitored, the fracture specimen would be formed of stainless steel.

Beams 14 and 16 are joined in the vicinity of the closed end 18 of the sensor assembly. The beams extend outwardly to an "open end" 20 of the assembly. The base 13 of the notch 12 which separates the beams is referred to as a notch root. A pre-formed crack (not shown in this figure) is formed in the notch root, as described in U.S. Pat. No. 4,677,855 (Coffin, Jr. et al.). In typical embodiments, current is passed through the specimen to establish a voltage drop across the crack. Voltage is measured by at least two pairs of probes (not shown in the figures) positioned at up to 99% of the pre-formed crack depth. The probes are usually positioned at opposite sides of the crack at an equal, known distance from the mouth of the crack. The measured voltage across each pair of probes is plotted as a function of the distance from the crack mouth of each probe pair. Data from the plot is used to determine the change in crack depth over time, as described in the Coffin patent.

Figure 2:
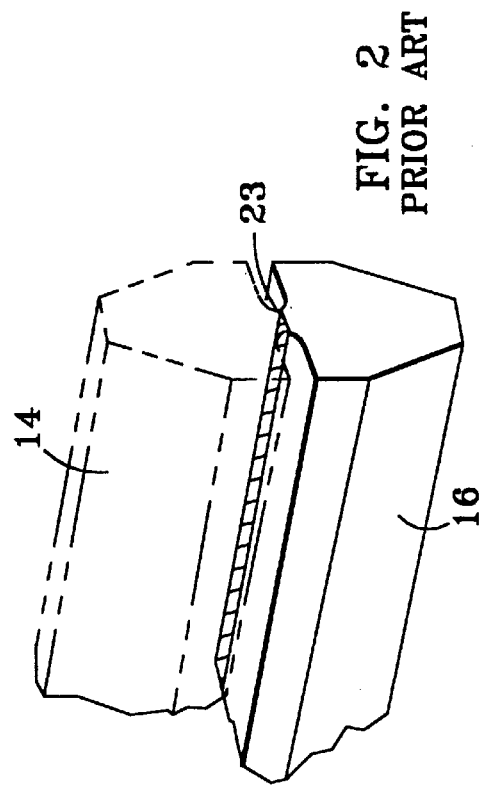
FIG. 2 is a partial end-view of the DCB sensor of FIG. 1.

With continued reference to the prior art embodiment of FIG. 1, beams 14 and 16 are joined in the vicinity of closed end 18 by a single ligament 22. For ease in illustration, the ligament has been "sliced" in half, with the top half being shown in phantom. Usually, the ligament is made of the same material as the beams. In fact, the ligament and the beams are typically machined to shape from a single block of metal. The end of the ligament which terminates at notch root 13 is the site of the pre-formed crack. The opposite end 23 of the ligament is also depicted in FIG. 2. In this figure, It can readily be seen how the ligament serves to attach beams 14 and 16 with each other.

As described previously, reducing the size of a conventional sensor assembly requires a reduction in the thickness of the ligament. However, an assembly like that of FIGS. 1 and 2 will be very difficult to manufacture if the ligament thickness is decreased. Moreover, the smaller assembly will be more flimsy and difficult to handle, e.g., during machining and cleaning, and during installation and removal from any apparatus or enclosure, e.g., an LPRM tube.

Figure 5:
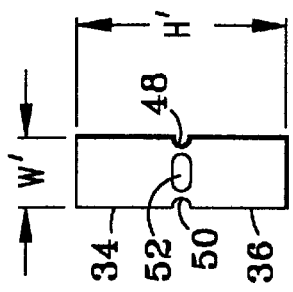
FIG. 5 is a right-side end view of the DCB sensor of FIG. 3.
Figure 3:
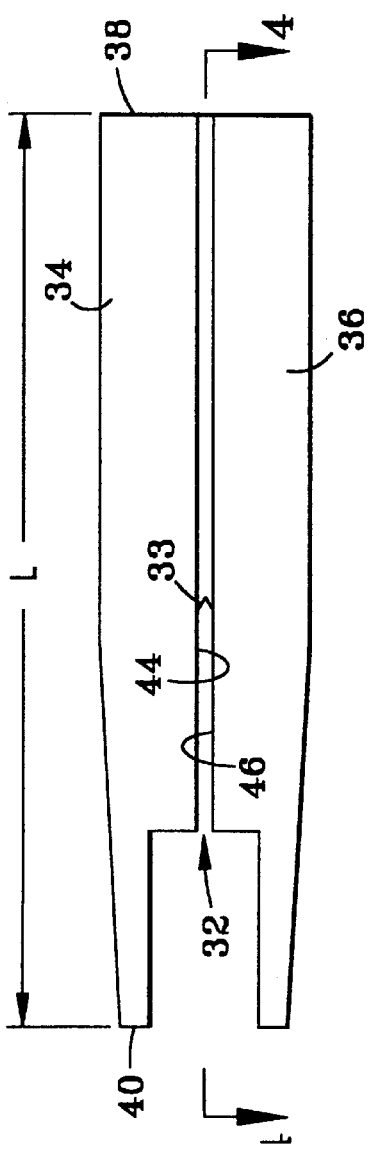
FIG. 3 is a front, elevational view of a DCB sensor of the present invention.
Figure 4:
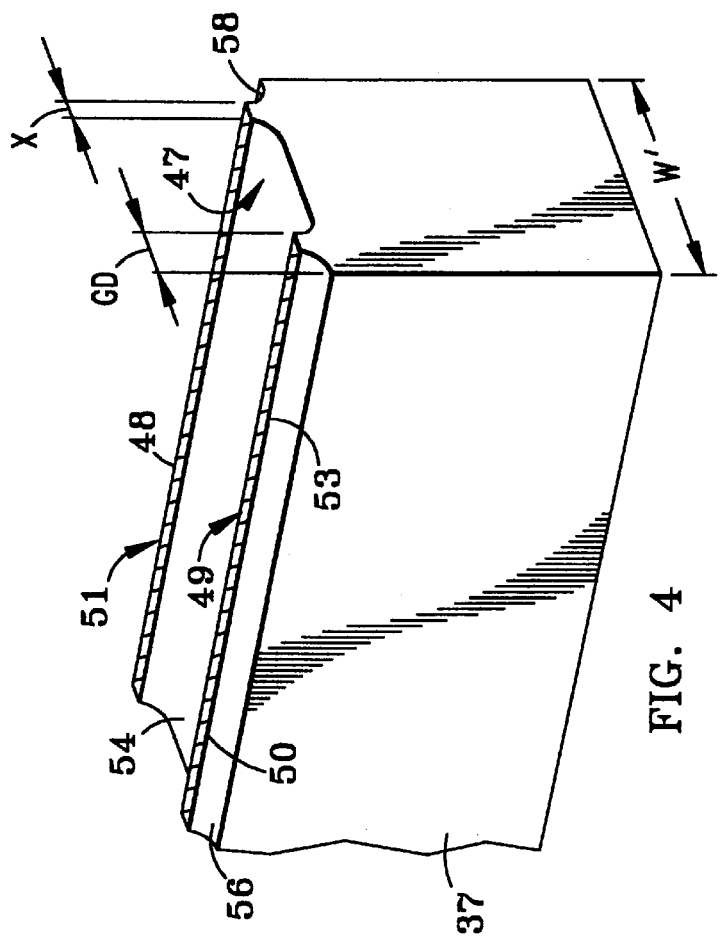
FIG. 4 is an isometric view of the DCB sensor of FIG. 3, through lines 4—4.

The DCB assembly depicted in FIGS. 3–5 was conceived according to the present invention. FIG. 3 is a front elevational view, showing notch 32 and notch root 33, which is the site of the pre-formed crack. The beams 34 and 36 extend outwardly from closed end 38 of the assembly to open end 40. Although the beams are depicted as generally parallel to each other in FIG. 3, they are induced to spread apart from each other in the open end area, during use of the assembly.

Many of the references set forth above describe various procedures for spreading apart the beams. Since this particular feature is not critical to the present invention, it need not be discussed in detail here. In general, there are two techniques for spreading the beams. First, a permanent wedge of some sort could be inserted between the beams at open end 40 to obtain a load which is sufficient for crack growth. This concept is described in many disclosures, such as the previously-referenced U.S. Pat. No. 4,677,855 (Coffin, Jr. et al.). Alternatively, an "actively-loaded" sample could be provided, i.e., where bellows or some other mechanism is used to urge the beams apart and then adjust the beams in response to measurements of beam displacement and stress intensity (e.g., see U.S. Pat. No. 5,386,442 of Diaz et al.).

In this invention, beams 34 and 36 are connected to each other along a portion of facing surfaces 44 and 46 by two parallel ligaments. FIG. 4 is an isometric view of the DCB sensor of FIG. 3, taken through lines 4—4. Ligaments 48 and 50 are spaced from each other on the facing surfaces of the beams. FIG. 5 is a right-side end view of FIG. 3, depicting the connection of the beams by the ligaments. A slot 52 is often present, representing the open area between the ligaments. However, the shape of the slot may vary considerably, depending, for example, on the shape of the beams; the dimensions of the ligaments; and the technique for fabricating the DCB assembly.

The depth of notch 32 is the longitudinal measurement that extends in a direction away from open end 40 and terminates at notch root 33, as seen in FIG. 3. (It should be apparent from viewing the figure that this depth can also be used to calculate the length over which the ligaments connect the two beams). The notch depth will depend on various factors, such as stress intensity and stress state characteristics, desired crack length, and tensile and bending loads to which the assembly will be subjected. Many of these factors are outlined in the art, e.g., the *Elastic & Plastic Fracture* text mentioned above. Those of skill in the art can readily consider these factors in determining an appropriate notch depth.

In some preferred embodiments, side grooves 56 and 58 are present, as shown in FIG. 4. Ligaments 48 and 50 have inner, substantially parallel surfaces 47 and 49, respectively, which face each other, and outer, substantially parallel surfaces 51 and 53, which are opposite the inner surfaces. In this exemplary embodiment, the side grooves are shaped as the outwardly-facing surfaces of the ligaments. The grooves may vary in size, shape, and length, as further discussed below. Curved side grooves like those shown in FIG. 4 can easily be made by use of a grinding wheel having a radius selected to provide such a curvature. The side grooves assist in keeping the direction of crack growth along a consistent direction and plane.

As mentioned above, the ligaments and the beams are usually formed from the same block of metal. However, in some embodiments, they could be separate pieces that are welded or brazed onto the facing surfaces of the beams. Thus, the ligaments could be made of practically any metal or metal alloy.

There is no restriction on the overall size of the DCB assemblies of the present invention, other than that which is specified by their intended end use. As mentioned previously, though, some preferred embodiments contemplate a size smaller than that of conventional DCB assemblies. For example, conventional assemblies typically have a beam width ("W" in FIG. 1) of about 1.1 cm to about 1.5 cm (these dimensions are measured at the greatest width, since the shape of beam is sometimes tapered, as shown FIG. 1). The assemblies based on this invention often have a beam width ("W'" in FIG. 5) of only about 0.25 cm to about 1.0 cm.

While conventional assemblies typically have a beam height ("H" in FIG. 1) of about 2.5 cm–3.5 cm, sensors of this invention often have a beam height ("H'" in FIG. 5) of only about 1 cm to about 2.4 cm. The smaller size of these DCB assemblies has several important advantages. In the case of a boiling water reactor, they can easily be fitted into an LPRM tube along with a tip tube monitor, as discussed above. (The length ("L" in FIG. 3) of the sensor is not as critical, since it is not usually the dimension which impedes fitting of the sensor into a cavity. Generally, though, the sensors of this invention have a length which is shorter than that of prior art sensors, i.e., a length of about 7 cm to about 14 cm, for example).

The width of each ligament in the sensor can depend on fabrication techniques and the type of metal being used, but will also depend on the environment in which the DCB assembly is being employed. (The width for the ligament as defined here is shown as dimension "X" in FIG. 4). The ligaments should be wide enough to provide the "connecting" strength necessary for a particular end use, e.g., if the assembly will be subjected to rigorous handling and/or operating conditions. However, they should not be so wide as to deform the beams when the latter are induced to spread apart. In general, the sum of the widths of both ligaments, i.e., "2X" is usually a value which is about 10% to about 50% of the width (W' in FIG. 4) of one of the beams, and preferably, about 20% to about 30% of the width of the beam.

The height of each ligament will depend to some extent on its width, and on various other factors mentioned previously. "Height" as used herein refers to the dimension perpendicular to the width dimension depicted in FIG. 4, starting from the planar beam surface 54, if such a surface were to be viewed as flat. In effect, the height would thus represent the distance that the beams are spaced apart from each other. In general, the height of each ligament for the reduced-size assemblies would be in the range of about 0.1 cm to about 0.5 cm, although that range may vary to some extent.

The ligaments are spaced from each other in a substantially parallel arrangement. The exact amount of spacing is not critical, and depends on various factors, such as the type of metal being used, the method employed to form the fracture specimen (e.g., the machining technique), and stress state mechanics considerations. The amount of spacing also depends on whether grooves 56 and 58 are present in the structure. (They are shown in the embodiment of FIG. 4). In general, the ligaments are preferably spaced as far apart from each other as possible. When side grooves are not present, the outwardly-projecting face of ligament 50 could be planar with beam surface 37, and the same would be true for ligament 48, relative to the analogous beam surface. This degree of spacing often provides the greatest amount of strength to the structure.

The degree of spacing can also be expressed as a function of the other relevant dimensions for the assembly. For example, when no side grooves are present, the maximum spacing would be (W'–2X), based on the dimensions depicted in FIG. 4. The minimum spacing is variable, but will usually be no smaller than the value (W'–3X). When the grooves are present, their depth will also be taken into account (side groove depth is shown as dimension "GD" in FIG. 4). In that instance, the spacing would preferably range from about (W'–2X-2GD) to about (W' -3X-2GD). The depth GD could be as large as ligament width X, or it could be considerably smaller, especially when width X is a considerably large value within the range set forth above.

It should be emphasized that DCB assemblies of the present invention do not have to be reduced in size. They can be as large as conventional DCB assemblies, or larger, as long as they include outwardly extending beams connected to each other along at least a portion of their facing surfaces by the spaced, parallel ligaments, as described above. The appropriate size of a particular DCB assembly will of course depend on various factors, e.g., where it is to be utilized, and what function it is to perform.

Methods for fabricating the DCB assembly are known in the art. Those skilled in metal-working and machining processes are familiar with equipment and techniques for forming the ligament-beam structure from a single block of metal. For example, various milling, shaping, and grinding procedures may be undertaken. Sometimes, electrical discharge machining or sawing could be used to form a rough shape, followed by milling and/or grinding to form the final shape.

The DCB assembly of this invention may include various elements commonly associated with such a device. The location and function of these elements are covered in many of the references set forth above, and need not be depicted in the drawing figures of this disclosure. As an example, the assembly (when functioning as a fracture specimen) usually includes sensor means positioned along or within the spaced beams. These sensor elements measure a voltage drop across the crack when a voltage is applied to the specimen. As described in the previously-referenced patent issued to Diaz et al., U.S. Pat. No. 5,349,869, the sensor elements can constitute pairs of probes disposed along the beams (e.g., along elements 34 and 36 in FIG. 3). Each probe pair is positioned at a different distance from the mouth of the crack, on opposite sides thereof. The probe pairs can be attached to the beams by weld-deposit techniques, for example. Techniques for applying current to the specimen, and using the resulting probe measurements of electrical potential to determine crack length over time, are described in various references, such as the Coffin et al patent, as discussed above.

As mentioned previously, the DCB assembly can also include means for exerting a load that urges the beams apart from each other at the open end (i.e., end 40 in FIG. 3). Such a technique is used in part to simulate the stress forces associated with stress corrosion cracking. The technique and associated components are well-known in the art and described, for example, in U.S. Pat. Nos. 5,417,116; 5,386,442; 5,378,429; 5,349,869; and 4,677,855, all referenced above. The particular stress-inducing mechanism is not critical to this invention. Sometimes, a wedge is forced within the notch to expand the crack. Clamps or bolts may be used to achieve a similar effect. An "actively-loaded" assembly as discussed above is sometimes preferred.

Various methods for calculating crack growth in the specimen (based on the electrical data from the sensors) are also well-known, as shown in U.S. Pat. No. 4,924,708 (Solomon et al.), for example. In the case of the boiling water reactors, crack growth data can be used to determine the effect of the water chemistry within the reactor. Based on that determination, the water chemistry can be modified, e.g., in regard to pH, oxygen level, impurity levels, and the like, to maintain an environment in which corrosion or other potential damage to the structures within the reactor vessel is minimized.

Various other features and details regarding DCB assemblies are well-known in the art, and could be used in conjunction with the features of the present invention. Many of the references set forth above refer to those features.

It should be apparent from the description provided above that another embodiment of this invention is directed to a corrosive environment measuring apparatus, comprising a double cantilever beam (DCB) assembly disposed in an aqueous portion of a reactor vessel. The assembly comprises:

a fracture specimen having a notch which defines first and second spaced, substantially parallel, outwardly extending beams, terminating at a closed end where crack growth occurs and extending to an open end;

wherein the beams are connected to each other along at least a portion of a facing surface of each beam by at least two parallel ligaments, spaced from each other on the facing surfaces of the beams. The apparatus can also include sensor means positioned along the beams for measuring a voltage drop, as described previously.

The DCB assembly can be disposed in a tube which is selectively lowered into the aqueous portion of the reactor vessel. The tube can be of any suitable shape, e.g., cylindrical or cruciform-shaped. The reactor could be of the nuclear-type, e.g., a BWR. In that case, the tube could be a local power range monitor tube, which may also accommodate a tip tube monitor.

While preferred embodiments have been set forth for the purpose of illustration, the foregoing description should not be deemed to be a limitation on the scope of the invention. Accordingly, various modifications, adaptations, and alternatives may occur to one skilled in the art without departing from the spirit and scope of the present invention. As but one example, the shape of the DCB assembly could be varied considerably. The beams would not have to be shaped as depicted in the drawings, as long as they could extend outwardly from a closed end, and included some sort of notch which is the site of a pre-formed crack. In these modified embodiments, the beams would still be connected by two, substantially parallel ligaments, as described previously.

All of the patents, articles, and texts mentioned above are incorporated herein by reference.

We claim:

1. A double cantilever beam assembly, comprising:

a fracture specimen having a notch which defines first and second spaced, substantially parallel, outwardly extending beams, terminating at a closed end where crack growth occurs, and extending to an open end;

wherein the beams are connected to each other along at least a portion of a facing surface of each beam by two substantially parallel ligaments, spaced from each other on the facing surfaces of the beams.

2. The double cantilever beam assembly of claim 1, wherein the ligaments are formed from the same material as the beams.

3. The double cantilever beam assembly of claim 2, wherein the material is selected from the group consisting of carbon steel, stainless steel, low alloy steel, zirconium-based alloys, and nickel-based alloys.

4. The double cantilever beam assembly of claim 2, wherein the ligaments and the beams are formed from the same block of metal.

5. The double cantilever beam assembly of claim 1, wherein the ligaments include inner parallel surfaces which face each other, and outer parallel surfaces opposite the inner surfaces, and wherein each outer surface comprises a side groove.

6. The double cantilever beam assembly of claim 1, wherein each ligament has a width, and the beam upon which the ligaments are disposed has a width, and the sum of the widths of the ligaments is about 10% to about 50% of the width of the beam.

7. A double cantilever beam assembly according to claim 1, having a width dimension and height dimension small enough to allow the assembly to be inserted into a local power range monitor tube along with a tip tube monitor.

8. The double cantilever beam assembly of claim 7, wherein the assembly width is in the range of about 0.25 cm to about 1.0 cm.

9. The double cantilever beam assembly of claim 8, wherein the assembly height is in the range of about 1 cm to about 2.4 cm.

10. The double cantilever beam assembly of claim 1, further comprising sensor means positioned along or within the beams, for measuring a voltage drop across the crack when a voltage is applied to the fracture specimen.

11. The double cantilever beam assembly of claim 1, further comprising means for exerting a load that urges the beams apart from each other at the open end, and a sensing mechanism to adjust the beams in response to measurements of beam displacement and stress intensity.

12. A corrosive environment measuring apparatus, comprising a double cantilever beam (DCB) assembly disposed in an aqueous portion of a reactor vessel, wherein the assembly comprises:

a fracture specimen having a notch which defines first and second spaced, substantially parallel, outwardly extending beams, terminating at a closed end where crack growth occurs, and extending to an open end;

wherein the beams are connected to each other along at least a portion of a facing surface of each beam by two, substantially parallel ligaments, spaced from each other on the facing surfaces of the beams.

13. The apparatus of claim 12, further comprising sensor means positioned along or within the beams for measuring a voltage drop across the crack when a voltage is applied to the fracture specimen.

14. The apparatus of claim 12, wherein the DCB assembly is disposed in a tube which is selectively lowered into the aqueous portion of the reactor vessel.

15. The apparatus of claim 14, wherein the reactor is a nuclear reactor, and the tube is a local power range monitor tube.

16. The apparatus of claim 15, wherein the tube is cruciform-shaped.

17. The apparatus of claim 15, wherein the local power range monitor tube also contains a tip tube monitor.

18. A sensor for measuring crack growth in response to a voltage drop thereacross comprising:

first and second beams fixedly joined together at a closed end by a pair of spaced apart integral ligaments, and spaced apart at an opposite open end to define a double cantilever beam assembly;

said beams being separated also by a notch extending to a root at said ligaments between said open and closed ends; and said notch root having a pre-formed crack across which said voltage drop is measurable.

19. A sensor according to claim 18 wherein said beams are collectively larger in sectional height than width, and said ligaments are laterally spaced apart across said beam width.

20. A sensor according to claim 19 wherein said beams are larger in length than said width, and said ligaments extend in part along said beam length.

* * * * *